(12) United States Patent
Kress et al.

(10) Patent No.: US 6,268,500 B1
(45) Date of Patent: Jul. 31, 2001

(54) SEPARATION OF 5-NITROQUINOLINE AND 8-NITROQUINOLINE

(75) Inventors: Thomas J. Kress, Greenwood; James P. Wepsiec, Indianapolis, both of IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 09/005,201

(22) Filed: Jan. 9, 1998

Related U.S. Application Data

(60) Provisional application No. 60/036,700, filed on Jan. 31, 1997.

(51) Int. Cl.$^7$ .................................................. C07D 215/18
(52) U.S. Cl. .............................................................. 546/180
(58) Field of Search ............................................... 546/180

(56) References Cited

FOREIGN PATENT DOCUMENTS

WO 94/24107    10/1994   (WO) .

OTHER PUBLICATIONS

Fieser LF and Herschberg EB. J. Am. Chem. Soc. vol. 62, pp. 1640–1645, 1940.*

Bradford et al. J. Chem. Soc. pp. 437–445, Mar. 1947.*

* cited by examiner

*Primary Examiner*—Evelyn Mei Huang
(74) *Attorney, Agent, or Firm*—Elizabeth A. Dawalt; William R. Boudreaux

(57) ABSTRACT

The present invention relates to a process for preparing 5-nitroquinoline hydrohalide comprising:

(A) heating a slurry comprising a mixture of nitroquinoline position isomer hydrohalide salts in wet dimethylformamide to form a solution;

(B) cooling the solution of Step (A) until a precipitate comprising 5-nitroquinoline hydrohalide is formed; and (C) collecting the precipitate.

11 Claims, No Drawings

SEPARATION OF 5-NITROQUINOLINE AND 8-NITROQUINOLINE

CROSS-REFERENCE

This application claims benefit of U.S Provisional Application No. 60/036,700 filed Jan. 31, 1997.

FIELD OF THE INVENTION

This invention relates to the art of synthetic organic chemistry. Specifically, the invention is a process to selectively separate compounds from a mixture, which compounds are useful as intermediates in syntheses of other organic compounds.

BACKGROUND OF THE INVENTION

When quinoline (Formula (1)) is nitrated,

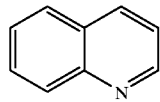

Formula (1)

a mixture of nitroquinoline position isomers is formed, which includes 5-nitroquinoline, 8-nitroquinoline and relatively small amounts of other nitroquinoline compounds.

5-nitroquinoline (Formula (2)) is a useful intermediate

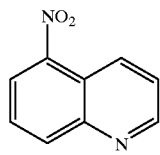

Formula (2)

for certain organic syntheses. Among other utilities, 5-nitroquinoline can be used as an intermediate in the synthesis of 10,11-cyclopropyldibenzosuberane derivatives as described in PCT Patent Application No. PCT/US94/04215 (Publication Number WO 94/24107).

8-Nitroquinoline (Formula (3)) is also a useful intermediate for certain organic syntheses.

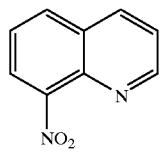

Formula (3)

Among other utilities, 8-nitroquinoline can be used in the synthesis of 8-aminoquinoline, which can be used in a number of syntheses of organic products, see e.g. EP 388619 (synthesis of pyridine-2,3-dicarboxylic acid), *Merck Index*, Tenth Edition, Merck & Co., 1983, pg. 707 (synthesis of 8-hydroxyquinoline) and *Merck*, pg. 1037 (synthesis of 1,10-phenanthroline).

The mixture of products obtained during the nitration of quinoline was disclosed in a report published in 1885 by Claus and Kramer in *Chem. Ber.*, (1885), 18, 1243. Seven years later, S. F. Dufton in *J. Chem. Soc.*, (1892), 61, 783, reported that by dissolving the mixture of nitro products in a large quantity of very dilute nitric acid and cooling, the 5-nitroquinoline isomer selectively separated as the nitrate salt. Later work by W. Meigan (*J. Prakt. Chem.*, (1908), 77, 472); R. P. Dickshoorn (*Rec. Trav. Chim.*, (1929), 48, 147); L. F. Fieser and E. B. Herschberg (*J. Am. Chem. Soc.*, (1940), 62, 1640); and V. M. Dziomko and I. A. Krasavin (*Khim Geterotsikl. Soedin.*, Sb. 1, Azotsoderzhashchie Geterosikly, 1967, 281; C.A., 1969, 70, 77748c), utilized this technique to prepare and separate quantities of 5-nitroquinoline and 8-nitroquinoline.

It must be noted that the use of a large volume of dilute acid is typically undesirable in any chemical process because of waste disposal issues.

What is needed are processes to selectively separate 5-nitroquinoline and 8-nitroquinoline from a mixture of nitroquinoline position isomers that provides a good separation of each isomer in relatively pure form, without the use of a large volume of dilute acid.

SUMMARY OF THE INVENTION

A first aspect of this invention is a process to separate 5-nitroquinoline hydrohalide from a mixture of nitroquinoline position isomer hydrohalide salts comprising:

(A) heating a slurry comprising a mixture of nitroquinoline position isomer hydrohalide salts in wet dimethylformamide to form a solution; and (B) cooling the solution of Step (A) until a precipitate comprising 5-nitroquinoline hydrohalide is formed.

A second aspect of this invention is a process to separate 8-nitroquinoline from a mixture of nitroquinoline position isomer hydrohalide salts comprising:

(i) adding a mixture of nitroquinoline position isomer hydrohalide salts to water or a mixture of water and a water-miscible liquid to form a slurry; and (ii) increasing the pH of the slurry of Step (i) until a precipitate comprising 8-nitroquinoline is formed.

A third aspect of this invention is a compound which is the hydrochloride salt of 5-nitroquinoline, namely 5-nitroquinoline HCl.

A further aspect of this invention is a process for preparing 5-nitroquinoline hydrohalide comprising:

(A) heating a slurry comprising a mixture of nitroquinoline position isomer hydrohalide salts in wet dimethylformamide to form a solution;

(B) cooling the solution of Step (A) until a precipitate comprising 5-nitroquinoline hydrohalide is formed; and (C) collecting the precipitate.

DETAILED DESCRIPTION OF THE INVENTION

The terms and abbreviations used in the instant examples have their normal meanings unless otherwise designated. Throughout this application, all percentages are weight percentages and all ratios are ratios based on weight.

The first aspect of the invention is a process to separate 5-nitroquinoline hydrohalide from a mixture of nitroquinoline position isomer hydrohalide salts. This process achieves good separation of 5-nitroquinoline hydrohalide from a mixture of nitroquinoline position isomer hydrohalide salts when wet dimethylformamide ("Wet DMF") is used as the solvent for the solution of step (A). Wet DMF describes dimethylformamide which has a small amount of water present in it. The amount of water present in Wet DMF is from about 0.5% to about 10%, preferably from about 0.5% to about 5% and most preferably about 1.25%. It has been found that when Wet DMF is used as the solvent, the selectivity of the separation is dramatically enhanced with the solid formed containing at least 99% 5-nitroquinoline hydrohalide and less than 1% other material(s). Wet DMF provided a high degree of selectivity of separation. Solvents other than Wet DMF either failed to produce a solid or produced a solid that still contained both 5-nitroquinoline and 8-nitroquinoline with the non-5-nitroquinoline portion of the solid being at least about 35%.

To obtain a good separation of 5-nitroquinoline hydrohalide from a mixture of nitroquinoline position isomer hydrohalide salts, the ratio of 5-nitroquinoline hydrohalide salt to the rest of the mixture should be at least about 4 (40%) to 6(60%). Preferably the ratio of 5-nitroquinoline hydrohalide salt to the rest of the mixture is at least about 5 (50%) to 5(50%). Of course, as the amount of 5-nitro-quinoline hydrohalide salt increases relative to the rest of the components in the mixture, the claimed separation process will continue to be effective. Therefore, although there is a practical lower limit (about 40%) to the amount of 5-nitroquinoline hydrohalide salt that should be present in the mixture in order to achieve an effective separation using the instant claimed process, there is no upper limit.

In order to obtain a mixture of nitroquinoline position isomer hydrohalide salts suitable for use in the instant claimed process, a mixture of nitroquinoline position isomers can be created and then contacted with a suitable hydrohalide to create nitroquinoline position isomer hydrohalide salts. A mixture of nitroquinoline position isomers can be made, using readily available commercial products, by nitration of quinoline using a combination of nitric acid and sulfuric acid. Procedures for nitration of quinoline using a combination of nitric and sulfuric acid are known in the literature (see, e.g., the references cited in the BACKGROUND OF THE INVENTION section of this application).

Preferable conditions, in terms of maximizing the yields of both 5-nitroquinoline and 8-nitroquinoline, are for the nitration reaction to be run at from about 95° C. to about 100° C. for about 1 to about 2 hours, using about 1.5 equivalents of nitric acid.

The typical mixture thusly created contains from about 40% to about 60% 5-nitroquinoline, from about 30% to about 50% 8-nitroquinoline with the remainder of the mixture containing other material(s) which can include non-reacted reagent(s), other nitroquinolines (such as 3-, 6-, and 7-nitroquinoline, and 5-hydroxy-6,8-dinitroquinoline) and other unidentified materials. Within these ranges, the amount of each component is such that the total percentage of all components in the mixture adds up to 100%. If desired, mixtures containing more than about 60% 5-nitroquinoline can be created by adding a suitable amount of 5-nitroquinoline to a mixture of nitroquinoline position isomers made by this procedure.

The precursor mixture for use in the process of the first aspect of this invention should contain at least about 40% 5-nitroquinoline, from about 30% to about 60% 8-nitroquinoline and at most about 30% other material(s). Preferably the mixture contains at most about 20% of other material(s), and most preferably the mixture contains at most about 10% of other material(s). A typical composition of a precursor mixture of nitroquinoline position isomers useful in the process of the first aspect of this invention is about 50%–51% 5-nitroquinoline, about 41%–46% 8-nitroquinoline, and about 3%–9% of other material(s).

In order to conduct the process of the first aspect of this invention, it is necessary to convert the 5-nitroquinoline in the mixture to its hydrohalide salt. For purposes of this application "hydrohalide salt" means the hydrochloride (HCl), hydrobromide (HBr) and hydroiodide (HI) salts. Of the hydrohalide salts, the HCl and HBr salts are preferred. The most preferred salt is the HCl salt.

The salt-forming reaction can be accomplished using many different techniques well known to those skilled in the art. The preferred way of conducting this procedure is to add a mixture of nitroquinoline position isomers to a suitable solvent to form a solution and then add a suitable hydrohalide to the solution. Suitable hydrohalides capable of forming hydrohalide salts include, but are not limited to, gaseous HCl, aqueous HCl or combinations thereof; gaseous HBr, aqueous HBr or combinations thereof; and aqueous hydroiodic acid. Suitable solvents for the salt-forming reaction include, but are not limited to, non-reactive organic solvents such as ethyl acetate, toluene, dimethylformamide, Wet DMF and acetonitrile. A preferred solvent for the salt-forming reaction is Wet DMF. Wet DMF is the preferred solvent for the salt-forming reaction because, for among other reasons, less hydrohalide has to be used and the separation of 5-nitroquinoline hydrohalide from the mixture can take place without having to remove the precipitate of nitroquinoline position isomer salts from the salt forming reaction solvent. Generally the amount of solvent needed to ensure solubility of the mixture of nitroquinoline position isomers is an amount such that there is a ratio of at least about 5 parts solvent to about 1 part mixture.

The sufficient amount of suitable hydrohalide capable of converting 5-nitroquinoline to its hydrohalide salt depends upon the solvent used in the salt-forming reaction. When Wet DMF is used as the solvent in the salt-forming reaction, then the amount of hydrohalide used should be about equivalent to or greater than the moles of 5-nitroquinoline present. It is preferred that the amount of hydrohalide used should be about equivalent to the moles of 5-nitroquinoline present. The amount of hydrohalide used should be about equivalent to the moles of 5-nitroquinoline present as it is not necessary to add enough hydrohalide here to convert all of the nitroquinoline position isomers present to their respective hydrohalide salts, rather it is only necessary to add sufficient hydrohalide to convert the 5-nitroquinoline to its hydrohalide salt in order to effect a good separation of 5-nitroquinoline hydrohalide later in the process. This is believed, without intending to be bound thereby, to be due to the fact that as the 5-nitroquinoline hydrohalide salt is formed, it precipitates out of the Wet DMF, which drives the equilibrium of the salt-forming reaction in favor of the formation of the less-soluble-in-Wet DMF 5-nitroquinoline hydrohalide salt as compared to formation of the more-soluble-in-Wet DMF 8-nitroquinoline and other nitroquinoline hydrohalide salts. Of course, regardless of the relative solubilities of the various nitroquinoline position isomer hydrohalide salts, a finite amount of other nitroquinoline position isomer hydrohalide salts (besides 5-nitroquinoline hydrohalide) will be formed during this salt forming reaction.

When a solvent other than Wet DMF is used for the salt-forming reaction, then the sufficient amount of suitable hydrohalide is about equivalent to or greater than the total moles of all nitroquinoline position isomers present. This is believed, without intending to be bound thereby, to be due to the fact that in a non-Wet DMF solvent there is not enough of a difference in solubility between 5-nitroquinoline hydrohalide and the other nitroquinoline position isomer hydrohalide salts to drive the reaction in favor of formation of the 5-nitroquinoline hydrohalide salt. Therefore, it is desirable to convert as much of the 5-nitroquinoline and other nitroquinoline position isomers present as possible to their respective hydrohalide salts, in order to ensure that as much of the 5-nitroquinoline as possible is converted to its hydrohalide salt. As is the case when the salt-forming reaction takes place in Wet DMF, in addition to 5-nitroquinoline hydrohalide, a finite amount of other nitroquinoline position isomer hydrohalide salts will be formed in this reaction Because more hydrohalide is preferably used during the salt-forming reaction when a non-Wet DMF solvent is used, there will be more nitroquinoline position isomer hydrohalide salts formed if a non-Wet DMF solvent is used, then if Wet DMF is used as the solvent.

Upon addition of the hydrohalide a precipitate is formed. This precipitate contains 5-nitroquinoline hydrohalide and some finite amount of other nitroquinoline position isomer hydrohalide salts. The formation of the precipitate changes the composition and appearance of the solution such that it is now a "slurry", with slurry being defined as a suspension containing a liquid phase and an insoluble solid phase.

If the salt forming reaction took place in Wet DMF then the separation process of the first aspect of this invention can be conducted by heating the slurry. If the salt forming reaction took place in a solvent other than Wet DMF, then the precipitate containing 5-nitroquinoline hydrohalide and some finite amount of other nitroquinoline position isomer hydrohalide salts must be collected, using standard techniques known in the art, and then added to a sufficient amount of Wet DMF to form a slurry. The sufficient amount of Wet DMF is an amount such that there is a ratio of at least about 5 parts solvent to about 1 part mixture.

The first step in the process of the first aspect of the invention is for the slurry to be converted to a solution. In order to form a solution the slurry is heated. The temperature the slurry is heated to ranges from about 50° C. to about 140° C., preferably from about 70° C. to about 120° C. and most preferably from about 95° C. to about 100° C. After heating to a temperature sufficient to form a solution, the solution is actively cooled using refrigeration or it is passively allowed to cool to a temperature such that a precipitate comprising 5-nitroquinoline hydrohalide is formed. Typically the precipitate comprising 5-nitroquinoline hydrohalide begins forming at a temperature of between about 75° C. and 80° C. Cooling is usually continued until a temperature of about 25° C. is reached.

The precipitate of 5-nitroquinoline hydrohalide may be collected by any known technique in the art, such as by decantation, centrifugation or filtering of the solution. By following the process of the first aspect of the instant invention it is possible to selectively separate 5-nitroquinoline hydrohalide from a mixture of nitroquinoline position isomer hydrohalide salts.

If the free base of 5-nitroquinoline is the desired product, then the 5-nitroquinoline hydrohalide may be converted to the 5-nitroquinoline free base by contacting the 5-nitroquinoline with a suitable inorganic or organic base including, but not limited to, NaOH, NaHCO$_3$, Na$_2$CO$_3$, triethylamine, trimethylamine and pyridine.

After the precipitate of 5-nitroquinoline hydrohalide has been collected, the remaining solution (also referred to as the "filtrate") contains nitroquinoline position isomers and some amount of their corresponding hydrohalide salts, with a new ratio of components in favor of the 8-nitroquinoline, because most of the 5-nitroquinoline has now been separated from the mixture. The ratio of 8-nitroquinoline and its hydrohalide salt to the rest of the solute of said solution (filtrate) is at least about 3 to 1. On a weight percent basis the solute of the solution (filtrate) contains at least about 75% 8-nitroquinoline and 8-nitroquinoline hydrohalide and no more than about 25% 5-nitroquinoline, 5-nitroquinoline hydrohalide and other material(s). This solution (filtrate) can be stored until needed or discarded in an environmentally safe manner.

If desired, 8-nitroquinoline (as a free base) can be separated from the solution (filtrate) remaining after the process of the first aspect has been conducted and the precipitate comprising 5-nitroquinoline hydrochloride has been collected, by following the process of the second aspect of this invention. The process of the second aspect of the invention will also work to separate 8-nitroquinoline (as a free base) from any solution containing a non-reactive solvent and a solute comprising at least about 75% 8-nitroquinoline or 8-nitroquinoline hydrohalide.

In order to separate and collect the 8-nitroquinoline from the solution, a sufficient amount of hydrohalide is added to cause a mixture of 8-nitroquinoline hydrohalide and 5-nitroquinoline hydrohalide and other trace amounts of certain nitroquinoline hydrohalide(s) to precipitate. The hydrohalide used can be any of the hydrohalides described for use in the process of the first aspect of this invention If the solution used in the process of the second aspect of the invention is created by following the process of the first aspect of this invention, then the hydrohalide used for Step (1) is preferably the same as the hydrohalide used in the previous salt-forming reaction. The sufficient amount of hydrohalide should be about equivalent to or in excess of the total number of moles of nitroquinolines present in the solution.

The precipitate of 8-nitroquinoline hydrohalide and 5-nitroquinoline hydrohalide can be collected using standard techniques known in the art. The first step of the process of the second aspect of the invention is for this precipitate to be added to water or a mixture of water and a water-miscible liquid to form a slurry. Said mixtures of water and a water-miscible liquid include, but are not limited to, water-methanol; water-ethanol; water-propanol, water-acetonitrile and water-tetrahydrofuran mixtures. The ratio of water to water-miscible liquids in these mixtures is at least about 90:10. Water is the preferred liquid component of this slurry.

The pH of the slurry so formed is about 1. The pH of the slurry is increased to cause precipitation of 8-nitroquinoline as a free base. Precipitation usually begins at a pH of about 2. Optimal precipitation takes place at a pH of about 3.5. The pH may be increased beyond about 3.5, however, doing this is counterproductive, because as the pH is increased beyond about 3.5, the precipitate contains more material that is not 8-nitroquinoline. Therefore, the preferred range of pH for this separation is from about 2 to about 5, and the more preferred pH is about 3.5 The pH is increased using a suitable base such as dilute aqueous sodium bicarbonate solution. The precipitate comprising 8-nitroquinoline, as the free base, can be collected using any suitable technique known in the art, such as filtration. The precipitate thusly formed has been found to contain over 95% pure 8-nitroquinoline. With additional crystallizations from a suitable solvent, such as isopropyl alcohol, the purity of the 8-nitroquinoline free base can be increased to over 99%.

The process of the first and second aspect of this invention may be conducted sequentially, with the process of the second aspect following the process of the first aspect, as described in the following text:

(A) heating a slurry comprising a mixture of nitroquinoline position isomer hydrohalide salts in wet dimethylformamide to form a solution;

(B) cooling the solution of step (A) until a precipitate comprising 5-nitroquinoline hydrohalide is formed;

(C) collecting the precipitate comprising 5-nitroquinoline hydrohalide from the resulting slurry of step (B);

(D) adding a sufficient amount of a suitable hydrohalide to the resulting filtrate of step (C) such that a precipitate is formed;

(E) collecting the precipitate of step (D);

(F) adding the precipitate of step (E) to water or a mixture of water and a water-miscible liquid to form a slurry; and (G) increasing the pH of the slurry of step (F) until a precipitate comprising 8-nitroquinoline is formed.

Another way of sequentially conducting the process of the first and second aspect of the invention is as follows:

a) adding a sufficient amount of a suitable hydrohalide to a solution comprising nitroquinoline position isomers in wet dimethylformamide, such that a precipitate is formed;

(b) heating the resulting slurry of step (a) to form a solution;

(c) cooling the resulting solution of step (b) until a precipitate comprising 5-nitroquinoline hydrohalide is formed;

(d) collecting the precipitate comprising 5-nitroquinoline hydrohalide from the resulting slurry of step (c);

(e) adding a sufficient amount of a suitable hydrohalide to the resulting filtrate of step (d) such that a precipitate is formed;

(f) collecting the precipitate of step (e);

(g) adding the precipitate of step (f) to water or a mixture of water and a water-miscible liquid to form a slurry; and (h) increasing the pH of the slurry of step (g) until a precipitate comprising 8-nitroquinoline is formed.

Another way of sequentially conducting the process of the first and second aspect of the invention is as follows:

(a) adding a sufficient amount of a suitable hydrohalide to a solution comprising nitroquinoline position isomers in a solvent that is not wet dimethylformamide, such that a precipitate is formed;

(b) collecting the precipitate of step (a);

(c) adding the precipitate of step (b) to wet dimethylformamide to form a slurry;

(d) heating the slurry of step (c) to form a solution;

(e) cooling the solution of step (d) until a precipitate comprising 5-nitroquinoline hydrohalide is formed;

(f) collecting the precipitate comprising 5-nitroquinoline hydrohalide from the resulting slurry of step (e);

(g) adding a sufficient amount of a suitable hydrohalide to the resulting filtrate of step (e) such that a precipitate is formed;

(h) collecting the precipitate of step (g);

(i) adding the precipitate of step (h) to water or a mixture of water and a water-miscible liquid to form a slurry; and (j) increasing the pH of the slurry of step (i) until a precipitate comprising 8-nitroquinoline is formed.

The following examples are illustrative only and are not intended to limit the scope of the invention in any way.

EXAMPLES

The terms and abbreviations used in the instant examples have their normal meanings unless otherwise designated. For example "° C." refers to degrees Celsius; "N" refers to normal or normality; "mmol" refers to millimole or millimoles; "g" refers to gram or grams; "d" refers to density, "min." refers to minutes, "mL" means milliliter or milliliters; "M" refers to molar or molarity; "HPLC" refers to high performance liquid chromatography; "mm" refers to millimeters; "cm" refers to centimeters; "nm" refers to nanometers; and "rt" refers to retention time.

Preparation I

Preparation of a Mixture of Nitroquinoline Position Isomers

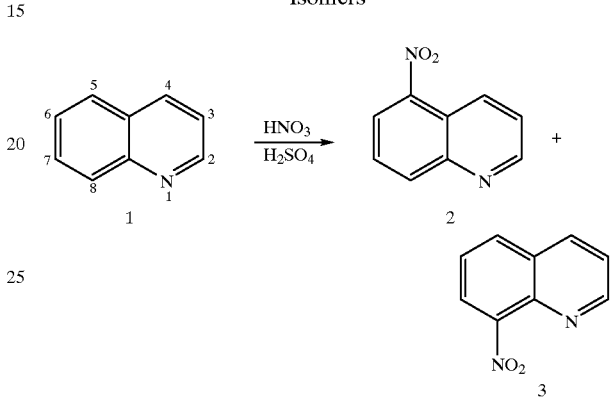

Quinoline (Formula (1), 12.9 g, 0.10 mole) was added dropwise over 5 min. with good agitation to a solution of 50 mL of concentrated sulfuric acid in a 250 mL round bottom flask. No attempt was made to control the exotherm and on this scale the final temperature was 77° C. The mixture was heated to 100° C. and 71% nitric acid (13.3 g, d. 1.42, 9.4 mL, 0.15 mole) was added at such a rate to keep the temperature between 100° C. and 110° C. Stirring was continued for an additional 30 minutes or until an HPLC (Zorbax® SB-C18 HPLC column, from Mac-Mod Analytical, Inc. of Chadds Ford, Pa. U.S.A.; dimensions 4½ mm (inside diameter) by 25 cm (length); HPLC conditions: 40:60 acetonitrile:water-0.5% ammonium acetate, 220 nm, flow 0.5 mL/min.) sample showed the reaction was complete. The mixture was cooled slightly and poured onto a mixture of 200 mL methylene chloride and 300 mL (by volume) of ice. The two phase mixture was placed in an ice bath and the temperature was kept below 25° C. while the pH was increased to 10 with concentrated ammonium hydroxide. The mixture was vacuum filtered through paper and transferred to a separatory funnel. The lower organic phase was separated and the aqueous layer was extracted with an additional 100 mL of methylene chloride. The combined organic layers were dried over magnesium sulfate, filtered and evaporated affording 15.8 g (91% yield) of a clear light amber oil which crystallized on standing. HPLC Analysis was conducted for 5-nitroquinoline and 8-nitroquinoline only: 45% 8-nitroquinoline (Formula (3), rt 9.0 min.) and 55% 5-nitroquinoline (Formula (2), rt 12.8 min).

Example I

Separation of 5-Nitroquinoline Hydrochloride from a Mixture of Nitroquinoline Position Isomers in Wet DMF The crude nitration mixture (15.8 g) created in Preparation I was dissolved in 80 mL of dimethylformamide (DMF)

containing 8 drops of water. Approximately 1.8 g (0.5 mole) of hydrogen chloride gas were added giving a cream colored precipitate. (Note: The amount of hydrogen chloride gas added could only be approximated as it was measured by weighing the flask.) The resulting slurry was heated to dissolution (95° C.–100° C.) to form a solution and this solution was cooled slowly to 25° C. Crystallization of a cream colored solid commenced at about 75° C.–80° C. The solid was collected by filtration, washed with ethyl acetate (2×25 mL) and dried and found to be 99.8% pure 5-nitroquinoline hydrochloride. The yield of 5-nitroquinoline hydrochloride was 7.8 g (37% overall yield from quinoline), mp 221° C.–222° C. Anal. Calcd for $C_9H_7N_2O_2Cl$: C, 51.32; H, 3.35; N, 13.30. Found: C, 51.59; H, 3.35; N, 13.00; m/z 174(100%), 175(15%), uv (EtOH) $\lambda_{max}$(log e) 310(3.79), 219(4.55).

Example II

Separation of 5-Nitroquinoline Hydrochloride from a Mixture of Nitroquinoline Position Isomers in Ethyl Acetate A crude nitration mixture (50 g) created in the manner of Preparation I was dissolved in 500 mL of ethyl acetate. Approximately 10.4 g (0.29 mole) of hydrogen chloride gas was added giving a yellow precipitate. (Note: The amount of hydrogen chloride gas added could only be approximated as it was measured by weighing the flask.) This precipitate was analyzed and found to contain 5-nitroquinoline hydrochloride and 8-nitroquinoline hydrochloride in a ratio of 51:41. The precipitate was collected by filtration and dried affording 54 g. The crude product was suspended in 270 mL of wet dimethylformamide (0.5 parts water in 99.5 parts dimethylformamide) to form a slurry. The slurry was heated to dissolution (95° C.–100° C.) to form a solution and this solution was cooled to 25° C. Crystallization of a cream colored solid commenced at about 85° C.–95° C. The solid was collected by filtration, washed with ethyl acetate (2×25 mL) and dried and found to be 99.0% 5-nitroquinoline hydrochloride and 0.41% 8-nitroquinoline hydrochloride. The yield of 5-nitroquinoline hydrochloride was 20.8 g (34.5% overall yield from quinoline).

Comparative Examples

Attempted Separation of a Mixture of Nitroquinoline Position Isomers Not Using Wet DMF as the Solvent Table I shows results of comparative examples (not examples of the invention) that attempted to separate and isolate 5-nitroquinoline hydrohalide from a solution containing nitroquinoline position isomers where Wet DMF was not used as the solvent. These comparative examples were conducted following this general procedure: a mixture of nitroquinoline position isomers is created according to the procedure of Preparation I and then the mixture is dissolved in ethyl acetate. Then hydrogen chloride gas, in an amount about equivalent to the total moles of 5-nitroquinoline and 8-nitroquinoline present, is added to form the hydrochloride salts of the nitroquinoline position isomers. The hydrochloride salts of the nitroquinoline position isomers precipitated together and this precipitate is collected and separated from the ethyl acetate. Separation of 5-nitroquinoline hydrochloride from this mixture is attempted by adding this precipitate to a solvent other than Wet DMF. The results of these attempts are shown in Table I. As the separation(s) did not occur as desired, no calculation(s) of the yield(s) is done.

TABLE I

COMPARATIVE EXAMPLES

| Comparative Example | Solvent | Result | % 5-nitro-quinoline-HCl | % 8-Nitro-quinoline-HCl |
|---|---|---|---|---|
| Ia | 70% $HNO_3$ | Clear soln. | — | — |
| Ib | 70% $H_2SO_4$ | Clear soln. | — | — |
| Ic | Con. HCl | Clear soln. | — | — |
| Id | acetonitrile (wet) | Yellow solid | 47% | 45% |
| Ie | acetonitrile (dry) | Yellow solid | 48% | 42% |
| If | DMF (dry) | Yellow solid | 62% | 35% |
| Ig | Nitro-$CH_3$ | Clear soln. | — | — |
| Ih | acetic acid | Clear soln. | — | — |

Example III

Isolation of 8-Nitroquinoline As A Free Base

To the combined wet dimethylformamide filtrate and ethyl acetate washes from Example I was added 2.55 g (0.7 mole) of hydrogen chloride gas affording a cream colored granular solid which was filtered, washed with ethyl acetate and after drying gave 9.82 g (47% yield) of a mixture composed of 17% 5-nitroquinoline hydrochloride and 82% 8-nitroquinoline hydrochloride (HPLC analysis). The mixture of hydrochloride salts (9.82 g) was suspended in 100 mL of water to form a slurry and the pH of the slurry increased to 3.5 with dilute aqueous sodium bicarbonate solution giving a cream colored solid. The solid was filtered, washed with 25 mL of cold water and dried giving 5.56 g (32%). HPLC analysis showed 96.3% 8-nitroquinoline and 3.7% 5-nitroquinoline. One crystallization from isopropyl alcohol (27 mL, 5 w/mL volumes) gave 4.8 g of 8-nitroquinoline as long stout needles, mp 88° C.–89° C. (99.6% purity by HPLC) and was identical in all respects to an authentic sample obtained from a commercial vendor.

We claim:

1. A process for preparing 5-nitroquinoline hydrohalide comprising:
   (A) heating a slurry comprising a mixture of nitroquinoline position isomer hydrohalide salts in wet dimethylformamide to form a solution;
   (B) cooling the solution of Step (A) until a precipitate comprising 5-nitroquinoline hydrohalide is formed; and
   (C) collecting the precipitate.

2. A process according to claim 1, Step (A) where the amount of water, in the wet dimethylformamide, is between 25 mg and 100 mg per gram of mixture of quinoline salts and the ratio, in grams, of dimethylformamide to the mixture of quinoline salts is between 4 and 6 to 1.

3. A process according to claim 1 where the solution of Step (A) is cooled to between 20° C. and 25° C.

4. A process according to claim 1 further comprising the initial step of adding a sufficient amount of a suitable hydrohalide to a mixture comprising nitroquinoline position isomers in a suitable solvent to form a mixture of nitroquinoline position isomer hydrohalide salts.

5. A process according to claim 4 where the suitable solvent is wet dimethylformamide to form the slurry of claim 1 step (A).

6. A process according to claim 5 where the amount of hydrohalide added is between 1 and 1.1 equivalents relative to the amount of 5-nitroquinoline present in the mixture.

7. A process according to claim 6 where the hydrohalide is gaseous hydrogen chloride.

8. A process according to claim 1 further comprising the step of:
   (D) reacting the precipitate of claim 1 step (C) with a suitable inorganic or organic base to form 5-nitroquinoline.

9. A process according to claim 1 further comprising:
   (D) adding a sufficient amount of a suitable hydrohalide to the filtrate from claim 1 step (C) to form a precipitate comprising a mixture of nitroquinoline hydrohalide salts;
   (E) forming a slurry comprising the precipitate from Step (D) in water or in a mixture of water and a water-miscible liquid;
   (F) increasing the pH of the slurry of Step (E) until a precipitate comprising 8-nitroquinoline is formed;
   (G) collecting the precipitate from Step (F).

10. A process according to claim 9, Step (F), where the pH is increased to between 3.0 and 4.0 with aqueous sodium bicarbonate.

11. A process according to claim 10 where the pH is between 3.45 and 3.55.

* * * * *